United States Patent [19]
Lohmeijer et al.

[11] Patent Number: 6,054,552
[45] Date of Patent: Apr. 25, 2000

[54] PROCESS FOR PREPARING ESTER AMIDES AND POLYESTERAMIDES

[75] Inventors: Johannes Hubertus G. M. Lohmeijer, Hoogerheide, Netherlands; Timothy E. Banach, Scotia; Daniel J. Brunelle, Burnt Hills, both of N.Y.; Gabrie Hoogland; Reimo Faber, both of Bergen op Zoom, Netherlands

[73] Assignee: General Electric Company, Pittsfield, Mass.

[21] Appl. No.: 09/134,308

[22] Filed: Aug. 14, 1998

[51] Int. Cl.$^7$ ............................. C08G 69/44; C08G 73/16
[52] U.S. Cl. ...................... 528/332; 528/272; 528/288; 528/291; 528/343
[58] Field of Search ..................... 528/272, 291, 528/292, 332, 343, 288

[56] References Cited

U.S. PATENT DOCUMENTS

| | | | |
|---|---|---|---|
| 4,209,607 | 6/1980 | Shalaby et al. | 528/291 |
| 4,226,243 | 10/1980 | Shalaby et al. | 128/335.5 |
| 4,501,879 | 2/1985 | Barbee et al. | 528/292 |
| 5,510,451 | 4/1996 | Gaymans et al. | 528/288 |
| 5,731,389 | 3/1998 | Bailly et al. | 528/288 |
| 5,852,155 | 12/1998 | Bussink et al. | 528/170 |

OTHER PUBLICATIONS

R.J. Gaymans and J.L. de Haan, Polymer, 34, 4360 (1993) The month in the date of publication is not available.

I. Goodman, Eur. Pol. J. 27, 515 (1991) The month in the date of publication is not available.

Hotten, R.W. Chem. Ind. Eng. 1957, 49, p. 1691 The month in the date of publication is not available.

Reinoud J. Gaymans and Antoinette C.M. van Bennekom, Polymer Preprints of the ACS, vol. 38 (2) Sep. 1997, pp. 402–403.

Meike C. Niesten, Krista Bouma, ReinoudJ. Gaymans, Polymer Preprints of the ACS. vol. 38 (2), Sep. 1997, pp. 480–481.

Krisa Bouma and Rainoud J. Gaymans, Polymer Preprints of the ACS. vol. 38 (2), Sep. 1997, pp. 486–487.

*Primary Examiner*—P. Hampton-Hightower

[57] ABSTRACT

In process for making a polyesteramide composition, an alkyl aryl terephthalate ester is formed from a dialkyl terephthalate by transesterification and then reacted with an alkyl diamine to form a bis-ester amide wherein the reaction product containing the bis-ester amide may be directly contacted with an alkyl diamine without the need for purification steps.

9 Claims, No Drawings

PROCESS FOR PREPARING ESTER AMIDES AND POLYESTERAMIDES

FIELD OF THE INVENTION

The present invention relates to a process for making a phenyl ester, the production of a bis-esteramide therefrom, and subsequent production of a polyesteramide resin.

BACKGROUND OF THE INVENTION

Polyesteramides, which have amide functionality incorporated into a polyester in a uniform fashion are of current interest for several reasons. At high levels of amide loading (>5%), the melting point and glass transition temperatures of the polymers can be significantly increased. See R. J. Gaymans and J. L. de Haan, Polymer, 34, 4360 (1993); (b) A. van Bennekom, "Fast Crystallizing Polyesteramides," Thesis for University of Twente (1995). Even at low levels of amide functionality (<1%), enhanced crystallization rates and increases in heat distortion temperature are observed. Unfortunately, it has proven difficult to prepare the polyesteramide polymers, due to side reactions observed upon introduction of a diamine into a polyester synthesis. For example, attempts to combine dimethyl terephthalate with butanediamine in the melt lead to significant levels of methylation on the amine (as much as 25%), which precludes efficient high molecular weight polymer formation upon introduction of a diol.

Currently, polyester amide polymers are prepared by a two step process, in which an intermediate bis-esteramide such as butylene-1,4-bis(p-carbomethoxy benzoyl amide) (T4T) is first prepared and purified, followed by utilization of that bis-esteramide as a comonomer with DMT and butanediol in the polymerization step.

Bis-esteramides have been prepared by several processes. Conversion of monomethyl-terephthalate to its acid chloride, followed by reaction with a diamine leads to high yields of bisesteramide. See I. Goodman, Eur. Pol. J. 27, 515 (1991). This route is not commercially viable due to limited availability of the monoacid, and to the necessity of its conversion to acid chloride.

Amide ester exchange of diamines on dimethyl terephthalate has been extensively studied by the Gaymans group at the University of Twente. See R. J. Gaymans and J. L. de Haan, Polymer, 34, 4360 (1993); A. van Bennekom, "Fast Crystallizing Polyesteramides," Thesis for University of Twente (1995) and Hotten, R. W. Chem. Ind. Eng. 1957, 49, p1691. According to the Gaymans process, lithium methoxide is used as the base in an amide ester exchange with excess dimethyl terephthalate (DMT). The use of relatively large amounts of lithium salts requires undesirable purification to remove them.

A presently preferred methodology for preparation of the bis-esteramide involves reaction of a 5–10 moles of DMT with butanediamine in a mixture of dry methanol/toluene using lithium methoxide as a catalyst at levels of up to 30% molar, based on diamine. This process is disclosed in U.S. Pat. No. 5,510,451 to Gaymans, et al. According to the patent a bisester diamide is prepared in a first step by reaction of a diamine with at least two-fold molar quantity of a diester of terephthalic acid, for example, dimethyl terephthalate. This reaction is generally carried out in the presence of a catalyst, for example, Li(OCH₃). A mixture of the diester diamide, a diol and optionally terephthalic acid, or a terephthalic acid derivative, may then be condensed to form a prepolymer. This prepolymer may finally be post-condensed to form a copolyester amide having the desired properties.

The above processes are, in general, complex and uneconomical, especially in view of the high amounts of catalyst utilized, sine the various intermediate products have to be isolated and purified. Hence, it is desirable to develop a simpler and more economical process which requires fewer process steps without complex purification of intermediate products.

SUMMARY OF THE INVENTION

Preparation of polyesteramides with high levels of amide functionality has required a discrete step for preparation and purification of a bisesteramide intermediate. Attempts at one-pot polymerizations have resulted in lower molecular weights than desired. As illustrated below, the primary side reaction which limits polymer chain growth is methylation of the diamine, resulting in chain termination. Although small amounts of these terminal groups can be tolerated when the level of amide functionality in the polyesteramide polymer is low, at higher amide loadings, the termination significantly limits building above Mw~40–50,000.

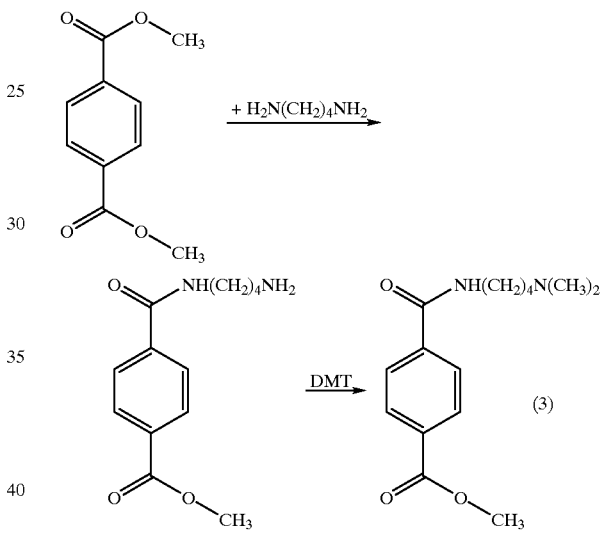

Several methods are available for preparation of the desired bis-esteramide intermediates, each with its limitations. Reaction in methanol or toluene/methanol mixtures affords yields of 80–90% T4T, but requires 5–10% lithium methoxide as a catalyst and long reaction times (24–48 hrs). Reaction in N,N-dimethylformamide (DMF)/toluene mixtures is significantly faster, requiring only 2–6 hr reaction times, but necessitates use of higher levels of lithium methoxide (20–30%), and also requires a dry reaction medium. Direct reaction of a diamine with the monoacid chloride gives the most convenient preparation, but is limited by the availability of the starting material.

We have shown that phenyl esters react via amide-ester exchange significantly faster than the methyl ester. We have found that polyesteramides can be prepared via a three-step, one-pot process, involving 1) transesterification of a dialkyl-terephthalate such as DMT to produce a mixture containing phenyl ester, 2) ester-amide exchange, to produce a mixture of bis-esteramide and a dialkyl terephthalate such as DMT, and 3) polymerization of the resulting mixture with butanediol. Alternatively, the bis-esteramide such as butylene-1,4-bis(p-carbomethoxy benzoyl amide) (T4T) product can be isolated after the step 2 ester amide exchange and used in polymerization reactions.

In accordance with one aspect of the present invention, there is provided a process for making a polyesteramide composition comprising forming an alkyl aryl terephthalate ester from a dialkyl terephthalate by transesterification, reacting said alkyl aryl aromatic phthalate ester with an alkyl diamine to form a bis-ester amide. The resulting bis-ester amide is preferably polymerized with a diol and a terephthalate ester to form a polyester amide.

In accordance with another aspect of the present invention, there is provided a process for making a polyesteramide composition comprising forming an alkyl aryl terephthalate ester from a dialkyl terephthalate by transesterification wherein said alkyl aryl aromatic phthalate is present in a resulting reaction product, contacting said reaction product with an alkyl diamine to react said alkyl aryl terephthalate portion in said reaction product with said alkyl diamine to form a bis-ester amide, and polymerizing said bis-ester amide with a diol and a dialkyl terephthalate to form a polyester amide.

In accordance with another aspect of the present invention, the amidation reaction product containing the bis-ester amide is directly reacted with the diol.

The above process represents a economically viable synthesis of bis-esteramides such as T4T.

Polyesteramide resins are disclosed in copending application Ser. No. 08/397,324 to Bailly, et al., filed Mar. 1, 1995. Blends of polycarbonate resins and polyesteramide resins have been disclosed in commonly owned and pending application Ser. No. 08/397,327 to Bailly, et al., filed Mar. 1, 1995. Blends of polyphenylene ether resins and polyesteramide resins have been disclosed in commonly owned and pending application Ser. No. 08/590,852 to Bailly, et al., filed Jan. 24, 1996.

DESCRIPTION OF THE PREFERRED EMBODIMENTS

Bis-esteramides such as butylene-1,4-bis(p-carbomethoxy benzoyl amide) [T4T] can be produced conveniently in a two-step, one pot reaction of dimethyl terephthalate. Conversion of dimethyl terephthalate first to a mono-phenyl ester via transesterification with, for example, diphenyl terephthalate, diphenyl carbonate, phenol, or phenyl acetate (Eqn. 1), followed by reaction with a diamine (Eqn. 2) leads to the desired bis-esteramide. Alternatively, monomethylterephthalate can be formed vial selective hydrolysis of DMT, followed by esterification to methyl phenyl terephthalate using phenol and boric acid. Because phenyl esters react significantly faster than methyl esters in the amidation step, the product is significantly purer than that obtained upon direct reaction of a diamine with dimethyl terephthalate. The bis-esteramides, which have limited solubility in many solvents can be isolated via filtration and washing, or the mixture of bis-esteramide, dimethyl terephthalate, and phenol can be used directly in polymerization reactions, with addition of a diol. Similarly, amidation reaction product containing the bis-ester amide may be directly reacted with the diol to form a polymer without the need for intervening purification steps.

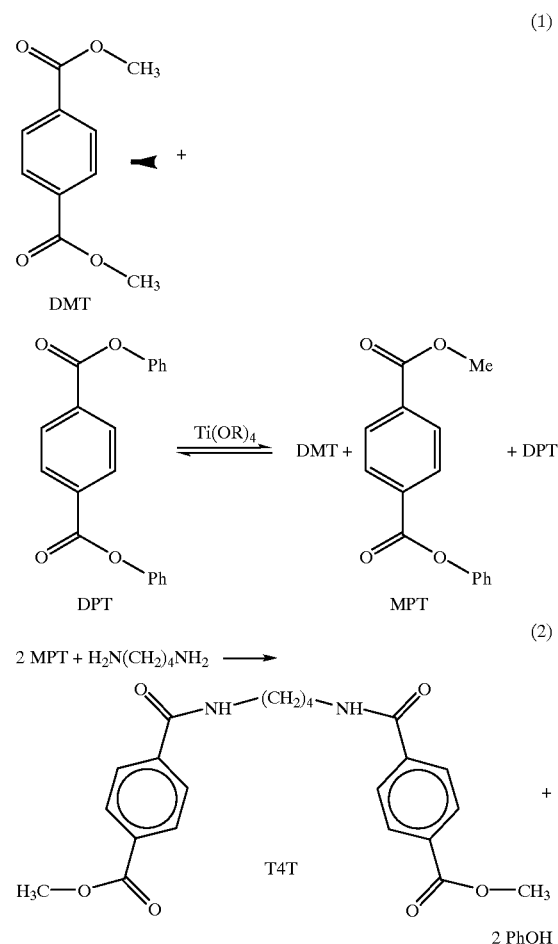

The resulting product of the transesterification reaction containing the phenyl alkyl ester is reacted via amide-ester exchange. In the case of the methyl phenyl terephthalate ester, the reaction is significantly faster than for the methyl ester. Next, the resulting reaction product containing the phenyl alkyl ester is reacted directly with a diamine via ester-amide exchange to produce the biester amide. The ester-amide exchange may be carried out by using the reaction product from the transesterification reaction in substantially unaltered form. Significant purification or alteration of the transesterification reaction product is avoided according to one aspect of the process of the present invention.

Transesterification to produce the phenyl esters can be carried out using a variety of reagents. The reaction can be catalyzed by titanates or by other common transesterification catalysts, and takes 15 min to 2 hours at reaction temperatures of 140–160° C. The reaction can be carried out neat or in an inert solvent such as xylene. Use of diphenyl terephthalate (DPT) leads directly to mixtures of DMT, DPT, and the desired mixed ester, methyl phenyl terephthalate (MPT) (Eqn. 1). Ideally, in order to obtain pure bisesteramide and avoid oligomerization reactions, pure MPT and a minimum of DPT would be desired. Transesterification produces a statistical mixture of products, and so use of excess DMT is required if significant quantities of DPT are to be avoided. Although no by-products are formed using DPT as the source of phenyl esters, that reagent is not readily commercially available. Other reagents which can be used for the transesterification include diphenyl carbonate and phenyl acetate. Diphenyl carbonate (DPC) is more readily available than DPT, and transesterifies at about the same reaction rate (Eqn. 4). The by-products of reaction, dimethyl carbonate (DMC) and methyl phenyl carbonate (MPC) must be removed prior to introduction of the diamine, to avoid urethane formation. Phenyl acetate is convenient, since it is commercially available, and the by-product which forms, methyl acetate, boils at about 60° C., and thus is easily removed from the reaction medium (Eqn. 5).

Another way to generate alkylphenylterephthalate is partial phenolysis of a dialkylterephthalate with phenol. Despite the low nucleophilicity of phenol, this route may still be attractive for use on an industrial scale, as phenol is readily available, and because potential carbonate- and/or acid-residuals that can react with amines are absent. Furthermore, phenol is generated again upon amidation of the alkylphenylterephthalate, and in principle can therefore be re-used in the phenolysis reaction of the dialkylterephthalate (Eqn. 6).

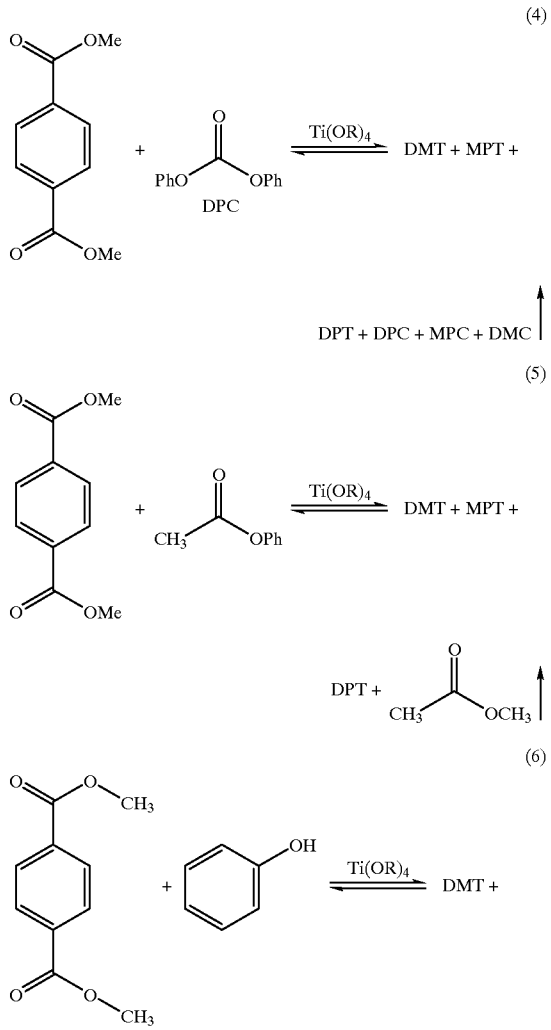

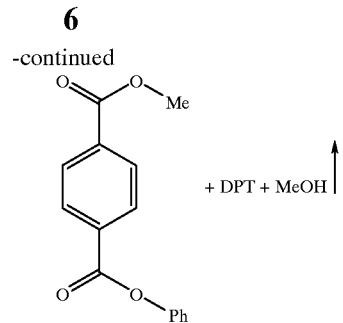

As with above described transesterification reactions utilizing DPT or DPC, an excess of DMT is needed to avoid the formation of significant quantities of DPT when preparing MPT. The reaction can be catalysed by titanates or other common transesterification catalysts and can be effected both in the melt or in a high boiling solvent, such as mesitylene. The use of a (refluxing) solvent is also advantageous to minimize losses of phenol and/or DMT by sublimation. Suitable reaction-temperatures are 170–190° C., other parameters to speed the reaction being reactant-concentration and effective removal of MeOH. An intert-gas flow through the reactor contents can help to drive the reaction into the thermodynamically unfavorable MPT direction. When a high boiling solvent is used, a hot water (70–80° C.) cooled condenser is very useful to remove methanol selectively, while keeping mesitylene and phenol in the reactor (Typical reaction times to convert 60–80% of the phenol to phenylester (using a DMT/Phenol molar ratio of 3/1) are 2–3 hours for melt reactions, 5–6 hours for 85% solids reactions and 8–10 hours for 30% solids reactions).

Because amidation of MPT is very fast, even at 30–60° C. in solution, substituted phenols with a lower nucleofugacity compared to phenol in the amidation-reaction but a higher nucleophilicity in the transesterification-reaction with e.g. DMT may be considered. This may bring conditions of both reactions closer to each other, which is beneficial for running them concertedly in a 1-pot system. How to activate phenols in this respect may be accomplished by methods known in the art, including possible deactivation by steric hindrance of ortho-substitution. Nucleophilicities can be varied over several orders of magnitude without affecting the steric requirements of the nucleophile by changing for instance the para-substituent from hydrogen to nitro or methoxy. Several phenols with electron-donating substituents, like p-methoxyphenol, p-cresol, 2,6-dimethylphenol and p-dimethylaminophenol were confirmed to be more reactive than phenol in esterification of DMT, though 2,6-dimethylphenol suffered clearly from steric hindrance. It was also proven that, besides the lower reactivity of the MPT-intermediates towards diamines, clean and fast conversion to T4T was possible.

It is known that the speed of nucleophilic substitutions can be influenced by the solvent that is used. Several transition state stabilizing solvents like diphenylether and dichlorobenzene were investigated. Their effect on the speed of the phenolysis reaction was apparant but of minor significance.

Once a mixture of MPT and DMT is produced, amide-ester exchange occurs readily (Eqn. 2). Whereas reaction of a diamine with DMT requires reaction temperatures of 170–175° C. to achieve useful rates, in the absence of catalyst, the phenyl ester reacts cleanly at 120° C. Since this temperature is significantly lower than that used for the reactions of methyl esters, far fewer by-products due to amine methylation are present. Since the product is cleaner, direct polymerization of the reaction product is possible, upon addition of butanediol and esterification catalyst. High molecular weight polymers have been achieved with 5% and 10% amide functionality.

Although direct polymerization of the crude product may be desirable, phenol will be liberated during the polymerization, since it is the by-product of the amide-ester exchange process and is still present in the reaction medium. If the presence of phenol is to be avoided, e.g. to improve color of the polymer or to prevent contamination of the condensate, isolation of the product T4T might be desirable. Since the amide-ester reaction can be carried out neat or in solution, various techniques can be used for purification, the simplest of which is filtration of the solid, insoluble bis-esteramide product. One technique for production of T4T is to 1) carry out the phenolysis, 2) perform amide-ester exchange, 3) filter off the T4T from the solvent/DMT/phenol mixture, 4) return the filtrate (solvent/DMT/phenol) into step #1, and 5) wash T4T with water to remove residual phenol.

The routes to T4T described in this letter so far depend upon the formation of a mixed terephthalate monomer, MPT via reaction of various reagents with excess DMT, in order to minimize formation of DPT. These reactions are non-selective with respect to the conversion of methyl esters to phenyl esters, forming statistical mixtures of products. These methods use low DMT conversion to prevent the extensive formation of diphenylterephthalate (DPT). DPT leads to the formation of oligomers (e.g., T4T4T) during amidation, which are not desireable. Unless the mixture of DMT/T4T can be used directly, such low-conversion reactions are economically unattractive. Therefore, a reaction which selectively forms phenyl esters without leading to formation of DPT (either through double reaction of DMT or through equilibration of MPT to DMT, MPT and DPT) would be highly desireable.

It is known in the literature that DMT can be selectively mono-hydrolyzed to monomethyl terephthalate (MMT) via treatment with KOH in toluene. See Hotten, R. W. Chem. Ind. Eng. 1957, 49, p1691. This reaction is highly efficient (yields >95%) and produces high purity MMT (purity=99+ %). The key requirement is therefore conversion of mono methyl terephthalate (MMT) to methyl phenyl terephthalate (MPT) without the equilibration of the product MPT. Quite unexpectedly, we found a reaction for converting MMT to MPT via reaction in the melt with diphenylcarbonate (DPC) and a catalyst. (Eqn 7) Though the reaction of DMT with DPC in solution is described herein, it was known that the acid would react directly and be selective for formation of MPT only. As shown by the data in example 16 below, this reaction cleanly forms MPT without equilibration or reaction at the methyl esters.

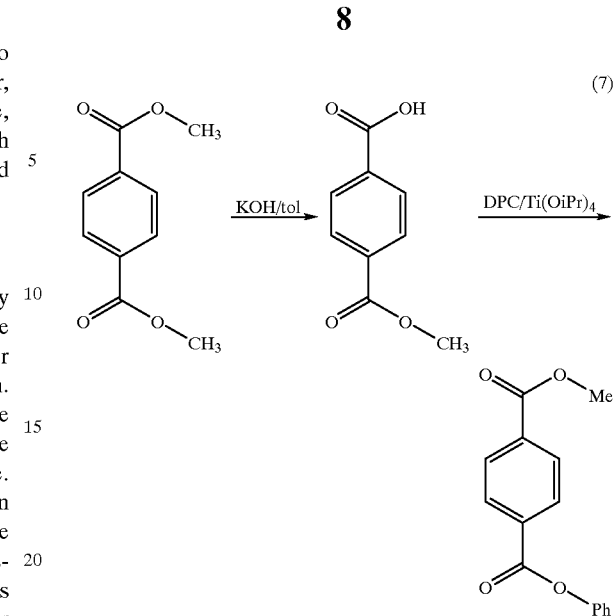

(7)

The reaction is sensitive to temperature, as shown by comparing entries 2,3,4 and 5 of Table 1. The temperature needs to be kept below 220° C. to prevent rapid equilibration of the product. The MMT:DPC ratio is also important as it appears that equilibration of the product MPT is inhibited by the presence of MMT. Thus, it is best to run the reaction near 210° C. with a slight excess of MMT (2%) to prevent formation of DMT and DPT.

A second procedure for forming MPT from MMT relies on direct esterification with phenol. Lowrence has shown that boric acid/sulfuric acid mixtures catalyze the preparation of phenyl esters from carboxylic acids and phenols, presumably via the intermediacy of triaryl borate.[9] Reaction of MMT with phenol in the presence boric acid and sulfuric acid leads directly to a high yield of MPT.

This procedure should be useful for preparation of bis-esteramides and polyesteramide polymers in general. Although dimethylterephthalate was used in all the examples, other ester starting materials could be used. Other phenyl esters could also be used for the transesterification, and a variety of transesterification catalysts are known. This procedure has been demonstrated with 1,2-ethylenediamine, 1,4-butanediamine, and 1,6-hexanediamine, producing T2T, T4T, and T6T respectively. Other diamines should react accordingly.

Generally, polyesteramide resins (PEA) are polymers comprising units represented by the amide formula (I):

(I)

and the ester formula (II):

(II)

Preferred PEA are substantially aliphatic PEA. Substantially aliphatic PEA refers to PEA containing at least about 10 mol %, preferably at least about 20 mol %, aliphatic residues in the PEA.

In a broad sense, polymers containing all ratios of formula (I) to formula (II) are possible and at the extreme where the amount of formula (II) in the polymers approaches zero, the polymers would be polyamide resins and conversely, where the amount of formula (I) in the polymers approaches zero, the polymers would be known as polyester resins. For the present invention, however, the ratio of units of formula (I) to units of formula (II) are about 1 to 1 or less, preferably about 1 to 2 or less, and most preferably 1 to 3 or less.

The amide formula (I) is generally derived from a reaction between:

(i) compounds having at least one amine group, represented by the general formula (III):

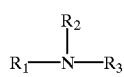

(III)

and (ii) compounds having at least one moiety having a carbonyl group, or a moiety capable of forming a carbonyl group, and capable of reacting with the amine of formula (III), and represented by the general formula (IV):

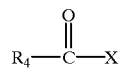

(IV)

In formula (III), each $R_1$, $R_2$, and $R_3$ can independently be a hydrogen, a $C_{1-20}$ alkylene or $C_{6-20}$ arylene group with the proviso that at least one of $R_1$, $R_2$, or $R_3$ is a leaving group, and with the proviso that at least one of $R_1$, $R_2$, or $R_3$ also contain at least one reactive moiety selected from the group consisting of amine, hydroxyl, carboxylic acid, imido, anhydride, ester, epoxy, carboxylic acid salt, or mixtures of the foregoing.

In formula (IV), $R_4$ is generally a $C_{1-20}$ alkylene or $C_{6-20}$ arylene group that contains at least one reactive moiety selected from the group consisting of amine, hydroxyl, carboxylic acid, imido, anhydride, ester, epoxy, carboxylic acid salt, or mixtures of the foregoing. Also in formula (IV), X is a leaving group capable of being displaced by a nucleophilic species, such as, for example, hydroxyl or amino.

In accordance with the principles of the present invention, typical carbonyl-containing compounds are represented by the formula:

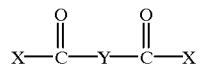

(V)

wherein Y is a divalent aliphatic or aromatic group containing at least two carbon atoms and one X is an alkoxy, such as methoxy or ethoxy and the other X is an aryloxy, such as, for example, phenoxy.

In the preferred embodiment, formula (III) is a lower alkyl diamine and formula (IV) is an phthalate or naphthalenedicarboxylate derivative. Preferred diamines are dimethylenediamine, tetramethylenediamine, hexamethylenediamine. Preferred phthalate and naphthalenedicarboxylate species, and lower alkyl and aryl esters of the foregoing and 2,6-naphthalenedicarboxylic acid as well as the corresponding lower alkyl and aryl naphthoate esters.

When the amine in formula (III) is a diamine, the amide of formula (I) can become a diamide comprising units represented by the general formula (VII):

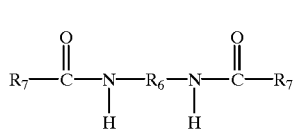

(VII)

wherein $R_6$ is a $C_{1-20}$ alkylene or $C_{6-20}$ arylene group and $R_7$ is as previously defined for $R_4$ in formula (IV).

Optionally, it is possible for the diamide or mixtures of diamides to have the formula (VIII):

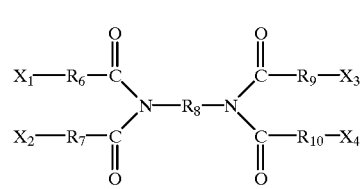

(VIII)

wherein $R_6$, $R_7$, $R_9$ and $R_{10}$ are, independently, aryl or alkyl groups, each having up to 12 carbon atoms, and wherein each $R_6$ and $R_7$ and each $R_9$ and $R_{10}$ may be connected to form a five or six membered ring structure; and each $X_1$, $X_2$, $X_3$ and $X_4$ is, independently, a moiety selected from hydroxy, carboxylic acid, a lower alkyl or aryl ester of a carboxylic acid, epoxy, carboxylic acid ammonium salt or an anhydride, or hydrogen provided that at least one of $X_1$ or $X_2$ and $X_3$ or $X_4$ are not hydrogen. $R_8$ is a $C_{1-20}$ alkylene or $C_{6-20}$ arylene group.

In a preferred embodiment, the carbonyl species of formula (IV) is a bis-carbonyl species and the resultant amide of formula (I) comprises units represented by the general formula (IX):

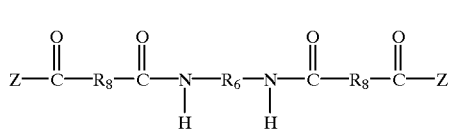

(IX)

wherein Z is a leaving group. $R_6$ is as previously defined in formula (VII), and each $R_8$ independently is generally $C_{6-20}$ alkylene, or $C_{6-20}$ arylene, or mixtures of the foregoing. Preferably $R_6$ is a 1,2-ethylene or 1,4-butylene group and each $R_8$ is para-phenylene.

When Z is an alkoxy or aryloxy group in formula (IX), the resultant formula can be referred to as a "bisester diamide" (referred to as BEDA hereinafter), e.g., a bisester diamide based on terephthalic acid or its derivative and amine or its derivative.

For purposes of simplicity and future reference in the examples, in formula (IX) when Z is methoxy, $R_8$ is p-phenylene, and $R_6$ is tetramethylene, the resulting compound is abbreviated as T4T-dimethyl. Similarly, in formula (IX) when Z is methoxy, $R_8$ is p-phenylene, and $R_6$ is hexamethylene or ethylene, the resulting compounds are abbreviated as T6T-dimethyl and T2T-dimethyl, respectively.

Preferred PEA have a substantially uniform structure and are derived from diacid derivatives, diols and diamines. The preferred PEA contain the general formula (X):

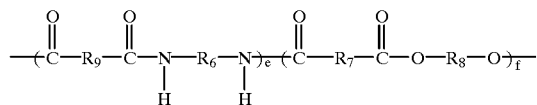

wherein $R_6$, $R_7$, $R_8$, and $R_9$ are independently $C_{1-20}$ alkylene or $C_{6-20}$ arylene, and wherein e and f are each an integer greater than or equal to 1. Preferably, $R_7$ and $R_9$ are the same and are arylene, preferably a para-phenylene radical and preferably $R_6$ and $R_8$ are the same (thus s=t in Pst defined below) and are $C_2$ to $C_6$ alkylene. It is preferable for e to be 1 or a mixture of 1 and higher integers wherein the fraction of said higher integers is less than about 15%, and more preferably less than about 10%.

In formula (X), when $R_7$ and $R_9$ are the same, preferably para-phenylene, the polymer comprising units of formula (X) can be referred to as a Pst, wherein s refers to the number of carbon atoms in $R_8$, and t refers to the number of carbon atoms in $R_6$. For example, the PEA derived from 1,4-butanediol and tetramethylenediamine as the diol and diamine respectively would be referred to as P44 and the PEA derived from 1,2-ethanediol and tetramethylenediamine would be referred to as P24. To designate the mole percentages of diamine based on the total of diamine and diol, the mole percentage of diamine is commonly designated as Pst-%. According to this nomenclature scheme, a PEA derived from 1,2-ethanediol and 1, 4-butylenediamine wherein the tetramethylenediamine is at a level of 20 mole percent, would be referred to as P24-20.

EXAMPLES

Example 1

Transesterification using diphenyl terephthalate melt reaction is carried out as follows. Dimethylterephthalate (9.97 g; 50 mmol) and diphenyl terephthalate (3.50 g; 10.0 mmol) were combined and heated to 220° C., at which point tetrakis-(2-ethylhexyl)titanate (0.25 ml of 1.0M solution in xylene; 0.25 mmole or 0.50 mole % vs DMT) was added. After 15 minutes, vpc analysis showed complete equilibration to a mixture of DMT, MPT, and DPT.

Example 2

Transesterification using diphenyl terephthalate by a solution reaction is carried out as follows. Dimethylterephthalate (9.97 g; 50 mmol) and diphenyl terephthalate (3.18 g; 10.0 mmol) were combined and heated to reflux in 50 mL of xylene, at which point tetrakis-(2-ethylhexyl)titanate (0.25 ml of 1.0M solution in xylene; 0.25 mmole or 0.50 mole % vs DMT) was added. After 1.5 hours, vpc analysis showed complete equilibration to a mixture of DMT, MPT, and DPT.

Example 3

Transesterification using diphenyl carbonate by solution reaction is carried out as follows. Dimethylterephthalate (9.97 g; 50 mmol) and diphenyl carbonate (2.14 g; 10.0 mmol) were combined and heated to reflux in 50 mL of xylene, at which point tetrakis-(2-ethylhexyl)titanate (0.25 ml of 10.0M solution in xylene; 0.25 mmole or 0.50 mole % vs DMT) was added. The by-product dimethyl carbonate was allowed to slowly distil, along with xylene as the bath temperature was increased to 175°. After 1.5 hours, vpc analysis showed complete equilibration to a mixture of DMT, MPT, and DPT, with only a trace of methyl phenyl carbonate remaining (less than 2%).

Example 4

Transesterification using phenyl acetate as a solution reaction is carried out in the following manner. Dimethylterephthalate (9.97 g; 50 mmol) and phenyl acetate (2.72 g; 20.0 mmol) were combined and heated to reflux in 50 mL of xylene, at which point tetraisopropyltitanate (75 µL, 0.25 mmole or 0.50 mole % vs DMT) was added. The by-product methyl acetate was allowed to slowly distil, along with xylene as the bath temperature was increased to 170°. After 1.5 hours, vpc analysis showed complete equilibration to a mixture of DMT, MPT, and DPT, with no trace of phenyl acetate remaining.

Example 5

The esteramide exchange is carried out as follows. The crude product from each of examples 1–4 was cooled to 120–140° C., and was treated with 1,4-butanediamine (10 mmol; 1.05 mL). Within 15 minutes, a precipitate began to form, which was identified as T4T by size exclusion chromatography (SEC). The reaction was complete after two hours, evident from the disappearance of the methyl phenyl terephthalate peak by vpc. SEC analysis showed formation of T4T as well as a small amount of oligomeric esteramide (~1–10%). T4T could be isolated by cooling to ambient temperature, dilution with $CH_2Cl_2$, and filtration, washing with more $CH_2Cl_2$.

Example 6

Transesterification using a phenol melt reaction was carried out as follows. Dimethylterephthalate (75.0 g; 0.38 mol) and phenol (12.0 g; 0.13 mol) were combined in an oil heated round-bottomed flask, equipped with magnetic stirrer, Dean-Start trap and nitrogen inlet. The mixture was heated to 190° C., at which point tetra-n-butyltitanate (0.2 g; 0.15 mole % vs DMT) was added. Nitrogen was allowed to pass through the melt to remove formed MeOH. After 3 hours, GLC analysis showed conversion to a mixture of DMT, MPT and DPT. The relative amounts of these products was dependent on the degree of conversion of phenol, which is determined by the efficiency of the MeOH removal. Typical phenol conversions of 60–80% are achieved, resulting in a DMT:MPT molar ration of 2.8–4.0:1. The amount of DPT vs. MPT was in the range of 1–5 mole %.

Example 7

Transesterification using phenol in a solution reaction was carried out as follows. Example 6 was repeated, but now 20 ml mesitylene was added next to the DMT and phenol. The Dean-Stark trap was replaced by a condenser with circulating water at a temperature of 80° C. The reaction mixture was heated at 180° C. and the nitrogen flow was adjusted for a gentle reflux. The main advantage of the addition of a solvent is that no sublimation of phenol and DMT occurs. The data (see example 6) about the DMT/MPT/DPT ratio of the melt reaction also apply to the solution reaction, but reaction times are longer, f.i. after 4 hours typical phenol conversions of 60–80% are achieved.

Example 8

Transesterification using p-methoxyphenol as a solution reaction was carried out as follows. Example 7 was repeated, but now the phenol was replaced by p-methoxyphenol (15.8 g; 0.13 mol). After 2.5 hours the reaction mixture did not contain any p-methoxyphenol as demonstrated by GLC; complete conversion to the MPT derivative resulted, with only 7% (vs MPT) of the DPT derivative being present.

Example 9

Esteramide exchange was carried out as follows. To the crude product from each of examples 6, 7 and 8 was added 200 ml mesitylene and the mixture was cooled to 140° C. After the addition of 1,4-butanediamine (3.4 g; 39 mmol), precipitation occurs within 15 minutes. After 2 hours, the reaction mixture was filtrated over a Büchner funnel that was heated with circulating water of 90° C. The residue, being T4T contaminated with some DMT, could be further purified by another hot filtration step. Alternatively, the T4T could be isolated by cooling to ambient temperature, dilution with $CH_2Cl_2$ and filtration, followed by another was step with $CH_2Cl_2$. The amount of T4T was 13.0 g, that is 82% of the diamine was converted to T4T.

Both HT-GLC and 1H-NMR analysis indicate that pure T4T is formed. Low-set GPC analysis showed the presence of 8% of T4T oligomers (mainly T4T4T) and perchloric acid titratables were 120 μeq/g. The titratables could be further reduced to 30–40 μeq/g by washing with (warm) MeOH, resulting in a monomer purity sufficient to obtain high molecular weight, high amide containing polyesteramides (see example 15).

Example 10

PBT with 5 mol % of butanediol replaced by butanediamine via incorporation of T4T obtained via transesterification using diphenylcarbonate. Dimethylterephthalate (244 g; 1.26 mol), diphenylcarbonate (54 g; 0.25 mol) and tetrabutyltitanate (1.45 g) were heated to 200° C. under nitrogen in a 2 l stainless steel reactor equipped with a torque measuring stirrer. Dimethylcarbonate was distilled off. After 1.5 hour the reactor was cooled to 160° C. and 1,4-butanediamine (17.6 g; 20 mol) was gradually added. A white precipitate formed.

After 1.5 hours, dimethylterephthalate (550 g; 2.83 mol), 1,4-butanediol (622 g; 6.91 mol) and tetrabutyltitanate (1.1 g) were added, and temperature was increased to 165° C. When 90% of the methanol (250 ml) had distilled off, temperature was increased by 2° C./min to 235° C. and by 1° C./min to 250° C. At 250° C. vacuum was gradually applied and stirring speed was gradually reduced. After about 1.5 hours and upon reaching maximum torque at lowest stirring speed, the reaction was terminated by breaking the vacuum with nitrogen. Under slight nitrogen-overpressure, the reactor was emptied via a bottom-valve. The molten strand was cooled in a waterbath and fed to a granulator for chopping into pellets.

Pellets were dried for 2 hours at 120° C. in vacuum prior to analyses. Weight average molecular weight determined with gel permeation chromatography (calibrated with polystyrene standards) was 75 kg/Mol. Perchloric acid titratables amounted to 15 μeq/g. Differential scanning calorimetry (heating to 300° C. and cooling by 20° C./min to room temperature) showed a crystallization maximum at 194° C. (enthalpy −45 J/g), and subsequent heating with 20° C./min a melting point at 221° C. (enthalpy 34 J/g). Proton-NMR pointed to a nitrogen content corresponding to 4.9% built-in diamide. 13C-NMR indicated that 90.1% of the diamide sequences are single, i.e. are flanked by diester- and not by other diamide-segments. In other words, the uniformity of diamide-segments with sequence-length equaling 1 is 90.1%.

Comparative Example 10a

PBT with 5 mol % of butanediol replaced by butanediamine via incorporation of T4T obtained using LiOMe catalysis. Dimethylterephthalate (88 g), N,N-dimethylformamide (DMF) (210 ml) and toluene (210 ml) were placed in an oil heated 1 liter glass reactor equipped with Dean-Stark trap, reflux cooler, stirrer and nitrogen inlet, and were heated under nitrogen to about 140° C. 1,4-diaminobutane (8 g) and $LiOCH_3$ (0.65 g) were added. The solution was stirred for about 4 hours during which a precipitate formed. The precipitate was hot-filtered, washed with hot toluene, then with hot methanol, and was dried at about 175° C. during 1 hour. Yield of T4T was 82%.

To a 1 liter glass reactor equipped with Dean-Stark trap, condenser, stirrer and nitrogen inlet was added dimethylterephthalate (337 g; 1.735 mol), afore mentioned T4T (37 g; 0.089 mol) and 1,4-butanediol (263 g). The contents were heated under nitrogen to 165° C. and allowed to dissolve while stirring. 0.46 ml $Ti(OC_4H_9)$ were added and methanol started to distill off. The temperature was raised to 235° C. in 30 minutes. After collection of 160 ml distillate, the Dean-Stark trap and condenser were replaced by a vacuum-line with cold trap. Vacuum was applied gradually to a pressure of about 5 mm Hg. When the viscosity started to rise the temperature was increased to 250° C. and the pressure reduced to about 0.1 mm Hg. The polymerization was discontinued when the melt started to wrap itself around the stirrer.

The polymer had a $M_w$ of 97 kg/Mol (vs.PS), perchloric acid titratables of 3 μeq/g, melting point of 221° C., crystallization point of 195° C., amide content 5.0% and uniformity of 92.4%.

Comparative Example 10b. Pure PBT

Dimethylterephthalate (200 g; 1.03 mol), 1,4-butanediol (186 g; 2.06 mol) and $Ti(OC_4H_9)_4$ (3.75 ml; 0.175 mol) were heated in a stainless steel reactor equipped with nitrogen inlet, stirrer and vacuum system to 160° C. and then with 1.5° C./min to 255° C. At 255° C. the pressure was gradually reduced to 15–20 mBar (15 min) and further to 0.1–0.4 mBar (60 min). The polymer was removed after cooling and breaking the vacuum.

The polymer had a $M_w$ of 93 kg/Mol (vs.PS), melting point of 222° C., and crystallization point of 186° C.

Examples 10, 10a and 10b show that the 3 polymers are close enough to be comparable in terms of crystallization rate, which is faster for the polyesteramides than for the pure PBT. More importantly, it is shown that hardly any differences exist between the polyesteramides of examples 10 and 10a, while the preparation in example 10 was far more easy than that in example 10a.

Above polymers (17 wt %) were extrusion-blended with polycarbonate (46 wt %, Lexan 125, General Electric), PBT (25 wt %, Valox 195, General Electric), rubber impact modifier (11 wt %), stabilizers/processing aids (1 wt %), and injection molded into test-bars, which had following properties:

| Material properties | PC + PBT from comp. examp. 10b | PC + PEA from comp. examp. 10a | PC + PEA from example 10 |
|---|---|---|---|
| Melt flow rate ISO1133 (at 250° C./2.16 kg/4' residence time | 12.85 ml/ 10 min | 14.08 ml/ 10 min | 19.34 ml/ 10 min |
| Vicat B temperature ISO306 heating rate 120° C./hr | 118.5 °C. | 129.0 °C. | 127.6 °C. |
| Tensile ISO527 at 50 mm/min Modulus | 2072 Mpa | 2161 MPa | 2221 Mpa |
| Yield stress | 53.4 Mpa | 55.3 MPa | 56.2 Mpa |

Above blends with polycarbonate show that the faster crystallization of the polyesteramides provides a higher Vicat-temperature, probably due to their faster phase seperation.

Example 11

PBT with 12 mol % of butanediol replaced by butanediamine via incorporation of T4T obtained by transesterification using diphenylcarbonate. Example 10 was repeated, but now 740 g (3.81 mol) dimethylterephthalate, 102 g (0.48 mol) diphenylcarbonate and 4.70 g tetrabutyltitanate were used, the amidation was carried out at 145° C. with 39 g, 1,4-butanediamine, and no additional dimethylterephthalate or new catalyst were added for the transesterification/polycondensation.
The polymer had a $M_w$ of 48 kg/Mol (vs.PS), perchloric acid titratables of 35 μeq/g, melting point of 230° C., crystallization point of 201° C., amide content 11.6% and uniformity of 92.5%.

Example 12

PBT with 14 mol % of butanediol replaced by butanediamine via incorporation of T4T obtained by transesterification using diphenylcarbonate. Example 10 was repeated with small changes to the amounts of the ingredients so as to attain a slightly higher amide content. The polymer had a $M_w$ of 35 kg/Mol (vs.PS), perchloric acid titratables of 45 μeq/g, melting point of 232° C.. crystallization point of 205° C., amide content 14.2% and uniformity of 90.1%.

Example 13

PBT with 11 mol % of butanediol replaced by butanediamine via incorporation of T4T obtained by transesterification using diphenylterephthalate. Example 11 was repeated, but now 697 g (3.59 mol) dimethylterephthalate, 143 g (0.45 mol) diphenylterephthalate, 4.7 g tetrabutyltitanate and no diphenylcarbonate were used.
The polymer had a $M_w$ of 60 kg/Mol (vs.PS), perchloric acid titratables of 20 μeq/g, melting point of 221° C., crystallization point of 198° C., amide content 11% and uniformity of 90.1%.

Example 14

PBT with 11 mol % of butanediol replaced by butanediamine via incorporation of T4T obtained by transesterification using diphenylcarbonate. Example 11 was repeated with 1.5× the amounts of initial ingredients, but after amidation the reactor was cooled down, its contents were crushed, slurried 3× in water/methanol (50/50 v/v) using a high shear mixer, washed with methanol and dried. 879 g of this material, containing only dimethylterephthalate and T4T, were added to the reactor together with butanediol (613 g; 6.81 mol) and tetrabutyltitanate (1.1 g), and polymerized as described in example 11. The polymer had a $M_w$ of 73 kg/Mol (vs.PS), perchloric acid titratables of 15 μeq/g, melting point of 232° C., crystallization point of 197° C., amide content 11.5% and uniformity of 90.1%.

This example indicates that it is beneficial to insert a purification step for obtaining high $M_w$ polyesteramides containing more than 5 mol % diamide.

Example 15

PBT with 11 mol % of butanediol replaced by butanediamine via incorporation of T4T obtained by transesterification using phenol. To a 2 l stainless steel reactor equipped with a torque measuring stirrer, Dean-Stark trap and nitrogen inlet was added dimethylterephthalate (686 g; 3.536 mol), T4T from Example 9 (194g; 0.471 mol) and 1,4-butanediol (613 g; 6.811 g). The contents were heated under nitrogen to 175° C. and allowed to dissolve while stirring. Methanol started to distill off due to residual Ti(OPh)4 in T4T which apparently was still active. When approximately 250 ml methanol had distilled off an additional quantity of 1.1 g Ti(OC$_4$H$_9$)$_4$ was added. Temperature was increased and polymer was made as described in example 10, having a $M_w$ of 84 kg/Mol (vs.PS), perchloric acid titratables of 19 μeq/g, melting point of 233° C., crystallization point of 201° C., amide content 11.7% and uniformity of 90.8%.

Example 16

Preparation of Monomethyl terephthalate. To a 3 L, 3-necked round-bottomed flask was charged DMT (213 g, 1.10 mol). The flask was fitted with a reflux condenser bearing a gas inlet connected to a N2-bubbler, a mechanical stirrer and a thermometer. Toluene (1.2 L) was added to the flask and the mixture was stirred while heating via a mantle until the internal temperature was 70° C. and a clear, colorless homogeneous solution had formed. To a 1 L Erlenmeyer flask was charged KOH (87% purity, 60.0 g, 0.930 mol) with a magnetic stirbar. Absolute methanol (342 mL) was added and the mixture was stirred to dissolve over ten minutes. The methanolic KOH solution was transferred to an addition funnel which was then attached to the 3 L flask. The base solution was added over 5 minutes with stirring but no heating. A fine white precipitate formed immediately, and the mixture was a thick slurry after 20 minutes of additional reaction time. Deionized water (1 L) was added to the reactor and the aqueous phase was separated in a separatory funnel and returned to the reactor. Concentrated HCl was added until the pH remained 2. During the addition a thick slurry formed of a white precipitate. The solid was collected on a fritted glass filter and washed twice with water. The solid was dried in a 110° C. vacuum oven for 16 hours. Yield of monomethyl terephthalate was 159.6 g (0.8868 mol), 95.4%.

Example 17

Melt reaction of MMT with DPC. Monomethylterephthalate (0.9008 g, 5.00 mmol), diphenyl carbonate (1.071 g, 5.00 mmol) and tetraisopropyl titanate (4.7 mg, 400 ppm as Ti) were charged to a 50 mL round-bottomed flask. The flask was equipped with a mechanical stirrer and a reflux condenser bearing a gas inlet connected to a N2 bubbler. Heating was accomplished by placing the flask in a 210° C. silicone oil bath whose temperature was maintained with a proportional heater controller. Samples were removed occasionally via cooling the flask slightly and withdrawing a small aliquot which was analyzed for MMT, MPT, DMT and DPT. Reactions were run either until a fixed amount of time or until 100% conversion of the MMT. Workup depended upon the desired use of the MPT; for solution amidations the reaction mixture was then dissolved in xylenes followed by reaction with 1,4-butanediamine as described in example 11.

TABLE 1

Typical Results for MMT + DPC.

| Entry | [Ti], ppm | Temp. °C. | Ratio MMT/DPC | time, h | % Conv. | % MPT | % DMT | % DPT |
|---|---|---|---|---|---|---|---|---|
| 1 | 200 | 200 | 1.00 | 3 | 6 | 100 | 0 | 0 |
| 2 | 400 | 200 | 1.00 | 4 | 16 | 90 | 7 | 3 |
| 3 | 400 | 210 | 1.00 | 4 | 95 | 86 | 7 | 7 |
| 4 | 400 | 220 | 1.00 | 4 | 100 | 47 | 30 | 23 |
| 5 | 400 | 230 | 1.00 | 4 | 100 | 47 | 22 | 31 |
| 6 | 400 | 210 | 1.02 | 8 | 72 | 79 | 11 | 9 |

Example 18

Preparation of T4T from MMT/PhOH. To a 25 mL round-bottomed flask was added recrystallized MMT (1.8142 g, 10.07 mmol), phenol (1.0779 g, 11.45 mmol, 1.14 equiv.), boric acid (33.1 mg, 0.535 mmol, 0.053 equiv.) and xylenes (10 mL). The flask was equipped with a magnetic stirbar and a Dean-Stark trap bearing a reflux condenser and a N2-inlet. The flask was stirred while heating via a 160° C. oil bath. After 15 min, the flask was removed from the oil bath and sulfuric acid (conc., 26.8 mL, 0.502 mmol, 0.050 equiv.) was added via an Eppendorf pipette. The flask was then replaced in the oil bath and allowed to reflux. After 27 h, 1H-NMR analysis showed that the MMT was 95.2% converted (86.6% MPT, 8.96% DPT and 4.45% DMT), at which point the reaction was cooled slightly, and transferred to a separatory funnel. The light yellow mixture was washed with 5% NaOH solution then twice with water. The organic phase was returned to the reactor were it was azeotropically dried. 1,4-Butanediamine (475.6 mL, 4.73 mmol) was added to the mixture which was stirred at reflux for 2.5 h. The resulting thick slurry was diluted to double its volume with xylenes and centrifuged in 12 mL glass tubes. The solid was collected and washed with 20 mL of 1:1 methanol:water, recentrifuged, then washed with 20 mL of methanol. After centrifuging a third time, the resulting light tan solid was dried in a 110° C. vacuum oven for 16 h. The yield was 1.79 g (92%) of T4T. GPC analysis revealed that it was 94% T4T with 6% higher oligomers.

What is claimed is:

1. A process for making a polyesteramide composition comprising forming an alkyl aryl terephthalate ester from a dialkyl terephthalate ester by transesterification wherein said alkyl aryl terephthalate ester is present in a resulting reaction product, contacting said reaction product with an alkylene diamine to react said alkyl aryl terephthalate ester portion present in said reaction product with said alkyl alkylene or arylene diamine to form a bis-ester amide, and polymerizing said resulting bis-ester amide with a diol to form a polyester amide.

2. A process according to claim 1 wherein said transesterification comprises reacting said dialkyl terephthalate with phenoxy derivative.

3. A process according to claim 2 wherein said phenoxy derivative is selected from the group consisting of diphenyl terephthalate, diphenyl carbonate, phenol, phenyl acetate, methyl phenyl carbonate, triphenylphosphite, and substituted phenols.

4. A process according to claim 3 wherein said reaction product comprising said alkyl aryl ester comprises by-products of said transesterification and removing said by-products prior to said reacting to forming said bis-ester amide.

5. A process according to claim 4 wherein said by products are volatilized from said transesterification reaction product.

6. A process according to claim 5 wherein said by-products comprise dimethyl carbonate and methyl phenyl carbonate.

7. A process according to claim 2 wherein said polymerization of said bis-ester amide comprises directly reacting the reaction product from said transesterification with a diol.

8. A process for making a polyesteramide composition comprising forming an alkyl aryl terephthalate ester from a dialkyl aromatic terephthalate by transesterification, reacting said alkyl aryl terephthalate ester with an alkylene diamine to form a reaction product containing a bis-ester amide.

9. A process according to claim 8 comprising separating said bis-ester amide from the reaction product and polymerizing said bis-ester amide.

* * * * *